US00PP18652P2

(12) United States Plant Patent
Valstar

(10) Patent No.: US PP18,652 P2
(45) Date of Patent: Mar. 25, 2008

(54) *CALATHEA* PLANT NAMED 'HGV04'

(50) Latin Name: *Calathea warscewiczii*
Varietal Denomination: HGV04

(75) Inventor: Oscar Valstar, Maasland (NL)

(73) Assignee: Gebr. Valstar Beheer BV, Maasland (NL)

( * ) Notice: Subject to any disclaimer, the term of this patent is extended or adjusted under 35 U.S.C. 154(b) by 0 days.

(21) Appl. No.: 11/478,053

(22) Filed: Jun. 29, 2006

(51) Int. Cl.
*A01H 5/00* (2006.01)

(52) U.S. Cl. ..... Plt./375

(58) Field of Classification Search ..... Plt./375
See application file for complete search history.

(56) References Cited

PUBLICATIONS

UPOV–ROM GTITM, Plant Variety Database, 2007/01, GTI Jouve Retrieval Software, citation for 'HGV04'.*

* cited by examiner

*Primary Examiner*—Kent Bell
*Assistant Examiner*—S. B. McCormick-Ewoldt

(57) ABSTRACT

A new cultivar of *Calathea* plant named 'HGV04' that is characterized by leaves that have a purple under side, a green upper side with yellow-green areas along the main and secondary veins and leaves with wavy margins.

1 Drawing Sheet

Botanical classification: *Calathea warscewiczii.*
Variety denomination: 'HGV04'.

BACKGROUND OF THE INVENTION

The present invention relates to a new and distinct cultivar of *Calathea* plant botanically known as *Calathea warscewiczii* and hereinafter referred to by the cultivar name 'HGV04'.

The new cultivar was discovered and selected as a single plant by the inventor in a cultivated area of Maasland, The Netherlands in 2002. 'HGV04' was discovered as a naturally occurring whole plant mutation within a population of unnamed *Calathea warscewiczii* plants.

Asexual reproduction by division of the new cultivar 'HGV04' was first performed in 2002 in Maasland, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Calathea* cultivar 'HGV04'.

1. *Calathea* 'HGV04' exhibits leaves that have a purple under side.
2. *Calathea* 'HGV04' exhibits leaves that have a green upper side with yellow-green areas along the main and secondary veins.
3. *Calathea* 'HGV04' exhibits leaves with wavy margins.

The closest comparison cultivars are plants of the species *Calathea warscewiczii.* The new cultivar 'HGV04' is distinguishable from plants of the species by the following characteristics:

1. 'HGV04' has leaves with lighter yellow-green areas around the main and secondary veins.

BRIEF DESCRIPTION OF THE DRAWING

The accompanying photograph illustrates the distinguishing traits of *Calathea* 'HGV04'. The plant in the photograph shows an overall view of a 4 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Calathea* cultivar named 'HGV04'. Data was collected in Maasland, The Netherlands from 4 month old greenhouse grown plants in 13 cm containers. The time of year was Winter and the average temperature was 20 degrees Centigrade during the day and 18 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'HGV04' has not been tested under all possible conditions and phenotypic differences may be observed with variations in environmental, climatic, and cultural conditions, however, without any variance in genotype.

Botanical classification: *Calathea warscewiczii* 'HGV04'.
Use: Ornamental.
Parentage: 'HGV04' is a naturally occurring whole plant mutation of an unknown *Calathea warscewiczii* cultivar.
Vigor: Moderate.
Growth rate: Moderate.
Growth habit: Moderately branching from base.
Plant shape: Broad inverted triangle.
Suitable container size: 13 cm diameter container.
Height: Average 23.5 cm in height.
Width: Average 37.5 cm in width.

Hardiness: USDA Zone 10.
Lower temperature tolerance: 12 degree Celsius.
High temperature tolerance: 37 degrees Celsius.
Propagation: Division.
Number of divisions or clumps per year: Average 1.
Time to produce a young plant: Approximately 30 days in the Summer and 45 days in the Winter.
Root system: Fine and fibrous.
Stem: No stems, Leaves grow directly from base, Average 2 clumps.
Foliage:

*Texture.*—Both surfaces slightly leathery.
*Leaf arrangement.*—Alternate.
*Compound or single.*—Single.
*Leaf shape.*—Ovate to broad elliptic.
*Leaf apex.*—Short apiculate.
*Leaf base.*—Obtuse.
*Leaf length.*—Average 18.3 cm in length.
*Leaf width.*—9.9 cm in width.
*Quantity of leaves per clump.*—Average 5 leaves per clump.
*Pubescence.*—Underside covered with dense hairs, 0.1 mm in length.
*Leaf margin.*—Entire, wavy, average 16 waves per leaf.
*Vein pattern.*—Pinnate.
*Young leaf color* (*upper surface*).—139A with margins 143A and 133A and narrow areas along main and secondary veins N144C.
*Young leaf color* (*lower surface*).—N77C.
*Mature leaf color* (*upper surface*).—139A and narrow areas along main and secondary veins N144A and N144D.
*Mature leaf color* (*lower surface*).—N77A.
*Vein color* (*lower surface*).—197A.
*Vein color* (*upper surface*).—146B.
*Leaf attachment.*—Petiolate.
*Petiole dimensions.*—Average 14.3 cm in length including geniculum, 5 mm in diameter below geniculum to 6 mm in diameter above clump.
*Petiole aspect.*—Round.
*Petiole surface.*—Covered with short hairs, length 0.5 mm, color 156A.
*Petiole color.*—137A, lighter towards the base 143A and 143B.
*Geniculum dimensions.*—Average 1.4 cm in length and 4 mm in diameter.
*Geniculum color.*—146A and 146B.
*Wing dimensions.*—Average 10.4 cm in length and 6 mm in diameter.
*Wing color.*—146B and 146C.
*Durability of foliage to stress.*—Moderate to high.

Flowers: Flowers have not been observed.
Disease and insect resistance: Plants of the new *Calathea* have not been observed for disease or insect resistance.

It is claimed:

1. A new and distinct variety of *Calathea* plant named 'HGV04' as described and illustrated.

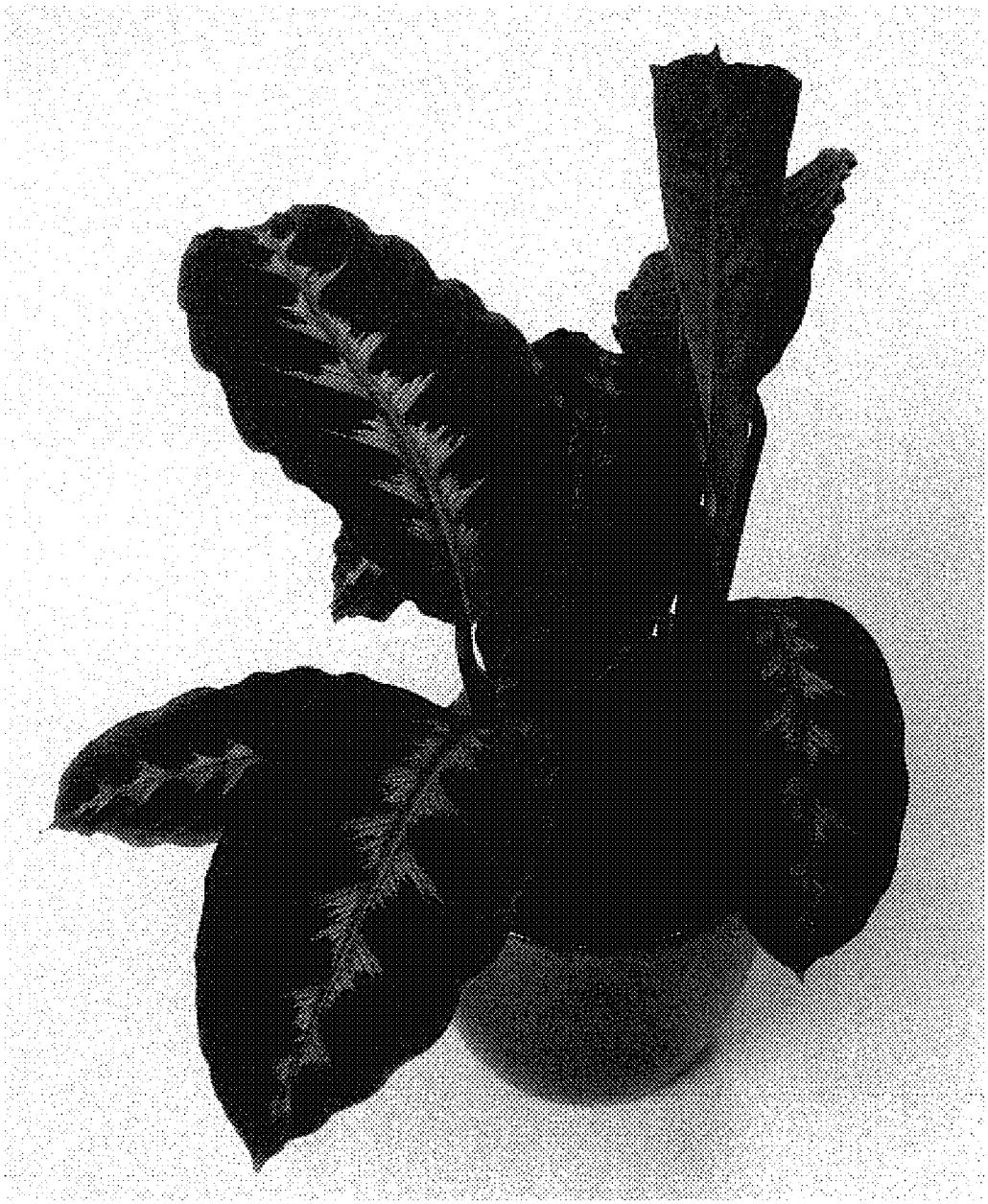

* * * * *